United States Patent [19]

Karjalainen et al.

[11] Patent Number: 4,544,664
[45] Date of Patent: * Oct. 1, 1985

[54] ANTIHYPERTENSIVE SUBSTITUTED IMIDAZOLE DERIVATIVES

[75] Inventors: Arto J. Karjalainen; Kauko O. A. Kurkela, both of Oulu, Finland

[73] Assignee: Farmos Group, Ltd., Turku, Finland

[ * ] Notice: The portion of the term of this patent subsequent to Jun. 8, 1999 has been disclaimed.

[21] Appl. No.: 396,000

[22] Filed: Jul. 7, 1982

[30] Foreign Application Priority Data

Jul. 10, 1981 [GB] United Kingdom ................ 8121333

[51] Int. Cl.$^4$ ................ A61K 31/415; C07D 233/56; C07D 233/64
[52] U.S. Cl. .................................... 514/396; 514/397; 514/400; 548/335; 548/336; 548/342
[58] Field of Search ............... 548/335, 336, 341, 342, 548/345; 542/458, 400, 468; 424/273 R; 514/397, 400, 396

[56] References Cited

U.S. PATENT DOCUMENTS 2,946,804 7/1960 Zaugg et al. ..................... 548/342
4,333,947 6/1982 Karjalainen et al. ............. 542/548
4,443,466 4/1984 Karjalainen et al. ............. 424/274

FOREIGN PATENT DOCUMENTS 0024829 3/1981 European Pat. Off. ........... 548/335
0034474 8/1981 European Pat. Off. ........... 548/335
0034473 8/1981 European Pat. Off. ........... 548/335

OTHER PUBLICATIONS

Kelley, J., et al., *J. Pharm. Sci.*, 70(3), 341–343, (1981).

Primary Examiner—Richard A. Schwartz
Attorney, Agent, or Firm—Armstrong, Nikaido, Marmelstein & Kubovcik

[57] ABSTRACT

The invention provides novel compounds of the formula:

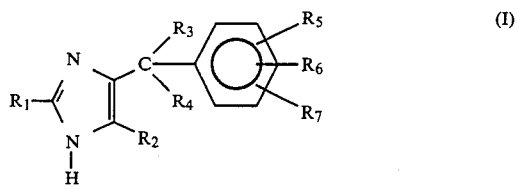

or

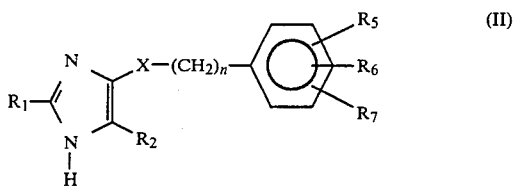

wherein the various substituents are defined herein below. Processes for the preparation of these compounds are described, as are novel pharmaceutical compositions comprising at least one of the compounds of their salts. The compounds and their non-toxic salts exhibit valuable pharmacological activity and are useful in the treatment of mammals, especially as antihypertensive agents. Furthermore, some of the compounds have proved to possess antithrombotic and diuretic activity. Antimycotic and antifungal properties have also been found.

12 Claims, No Drawings

ANTIHYPERTENSIVE SUBSTITUTED IMIDAZOLE DERIVATIVES

DESCRIPTION

The present invention relates to substituted imidazole derivatives and their non-toxic, pharmaceutically acceptable acid addition salts, and their preparation, to pharmaceutical compositions containing the same, and to their use.

The imidazole derivatives of the present invention have the general formula:

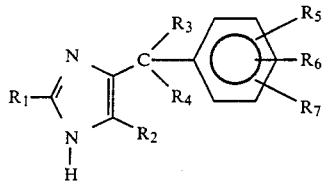
(I)

or

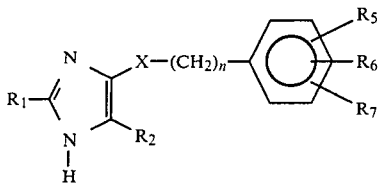
(II)

wherein $R_1$ is H, an alkyl of 1 to 4 carbon atoms, e.g. methyl or —CH$_2$OH; $R_2$ is H or CH$_3$; $R_3$ is —CH$_3$, —CH$_2$CH$_3$, —CH$_2$CH$_2$CH$_3$,

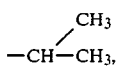

—CH$_2$CH$_2$CH$_2$CH$_3$, —CH$_2$CH=CH$_2$, or

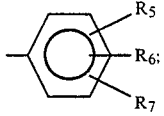

and $R_4$ is H or OH; or $R_3$ and $R_4$ together represent =CH$_2$, =CH—CH$_3$, =CH—CH$_2$—CH$_3$,

or =CH—CH$_2$CH$_2$CH$_3$; X is

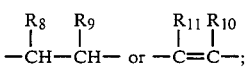

$R_5$, $R_6$, and $R_7$, which can be the same or different are H, —CH$_3$, —CH$_2$CH$_3$, halogen, OH or —OCH$_3$ or $R_5$ is hydrogen and $R_6$ and $R_7$ together form an —O—CH$_2$—O—bridge between two adjacent carbon atoms in the phenyl group; —CHR$_8$— is —CH$_2$—, —CH(CH$_3$)—, —CH(—CH$_2$CH$_3$)—, —CH(—CH$_2$CH$_2$CH$_3$)—,

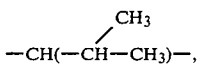

—CH(—CH$_2$CH$_2$CH$_2$CH$_3$)— or >C=CH$_2$, >C=CH—CH$_3$, >C=CH—CH$_2$CH$_3$,

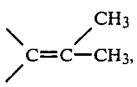

>C=CH—CH$_2$CH$_2$CH$_3$; $R_9$ is H, —CH$_3$, —CH$_2$CH$_3$, —CH$_2$CH$_2$CH$_3$,

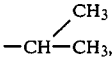

—CH$_2$CH$_2$CH$_2$CH$_3$ or OH; $R_{10}$ is H, —CH$_3$, —CH$_2$CH$_3$, —CH$_2$CH$_2$CH$_3$,

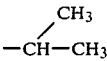

or —CH$_2$CH$_2$CH$_2$CH$_3$; $R_{11}$ is H, —CH$_3$, —CH$_2$CH$_3$, —CH$_2$CH$_2$CH$_3$,

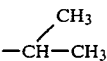

or —CH$_2$CH$_2$CH$_2$CH$_3$; n is 0 to 4; provided that when $R_4$ is OH, $R_1$ is H or CH$_3$ and $R_3$ is

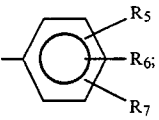

then $R_5$, $R_6$ and $R_7$ are not all simultaneously hydrogen;

when $R_1$, $R_2$ and $R_4$ all are hydrogen and $R_3$ is

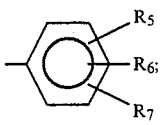

then $R_5$, $R_6$, $R_7$ are not all simultaneously hydrogen; $R_8$ and $R_9$ are not simultaneously hydrogen; and $R_{11}$ and $R_{10}$ are not simultaneously hydrogen.

Because of the tautomerism in the imidazole ring the compounds of the general formula I and II are 4(5)-substituted imidazole derivatives.

The non-toxic pharmaceutically acceptable acid addition salts of these compounds are also within the scope of the invention.

The compounds of the formula (I) and (II) form acid addition salts with both organic and inorganic acids. They can thus form many pharmaceutically usable acid addition salts, as, for instance, chlorides, bromides, sulfates, nitrates, phosphates, sulfonates, formates, tartrates, maleates, citrates, benzoates, salicylates, ascorbates and the like.

The invention includes within its scope pharmaceutical compositions comprising at least some of the compounds of formula (I) or (II) or a non-toxic, pharmaceutically acceptable salt thereof, and a compatible pharmaceutically acceptable carrier therefor.

The invention provides, for example, the following specific compounds of formula (I):
4-[α,α-bis(2-methylphenyl)hydroxymethyl]imidazole
4-[[α-(2-methylphenyl)]-2-methylbenzyl]imidazole
4-(α-phenylbenzyl)-5-methylimidazole
4-[[α-(2,6-dimethylphenyl)]-α-methyl]hydroxymethyl]imidazole
4-[[α-(2,3-dimethylphenyl)]-α-methyl]hydroxymethyl]imidazole
4-[α,α-bis(2-methylphenyl)hydroxymethyl]-5-methylimidazole
4-[[α-(2-methylphenyl)]-2-methylbenzyl]-5-methylimidazole
4-[(α-methyl)-2,6-dimethylbenzyl]imidazole
4-[(α-methyl)-2,3-dimethylbenzyl]imidazole
4-[(α-ethyl)-3-methylbenzyl]imidazole
4-[(α-butyl)-2,3-dimethylbenzyl]imidazole
4-[(α-methyl)-2,3-dimethylbenzyl]-2-methylimidazole
4-[(α-propyl)-2-methylbenzyl]imidazole
4-[(α-methyl)-2-methylbenzyl]imidazole
4-[(α-methyl)-2,5-dimethylbenzyl]imidazole
4-[α-ethyl-α-(3-methylphenyl)-hydroxymethyl]imidazole
4-[α-butyl-α-(2,3-dimethylphenyl)-hydroxymethyl]imidazole
4-[α-methyl-α-(2,3-dimethylphenyl)-hydroxymethyl]-2-methylimidazole
4-[α-propyl-α-(2-methylphenyl)-hydroxymethyl]imidazole
4-(α-methyl-2-chlorobenzyl)imidazole
4-[α-methyl-α-(2-methylphenyl)-hydroxymethyl]imidazole
4-[α-methyl-α-(2,5-dimethylphenyl)-hydroxymethyl]imidazole
4-[α,α-bis-(2,3-dimethylphenyl)hydroxymethyl]imidazole
4-[α-(2,3-dimethylphenyl)-2,3-dimethylbenzyl]imidazole
4-[(α-ethyl)-2,6-dimethylbenzyl]imidazole
4-[(α-ethyl)-2,3-dimethylbenzyl]imidazole
1-(4-imidazolyl)-1-(2,3-dimethylphenyl)ethylene
1-(4-imidazolyl)-1-(2,6-dimethylphenyl)ethylene
1-(4-imidazolyl)-1-(2,3-dimethylphenyl)propene
1-(4-imidazolyl)-1-(2,3-dimethylphenyl)pentene The following specific compounds of formula (II):
4-[2-(2,6-dimethylphenyl)-1-methylethyl]imidazole
4-[2-(2,6-dimethylphenyl)propyl]imidazole
4-[2-(2,3-dimethylphenyl)propyl]imidazole
4-[2-(2,6-dimethylphenyl)-1-methylpropyl]imidazole
4-[2-(2,6-dimethylphenyl)-2-hydroxyethyl]imidazole
4-(2-phenylpropyl)imidazole
4-[2-(2,6-dimethylphenyl)-1-methylethenyl]imidazole
4-[2-(2,6-dimethylphenyl)-1-propenyl]imidazole
4-(2-methyl-4-phenyl-1-butenyl)imidazole
4-[2-(4-chlorophenyl)-1-methylpropyl]imidazole
4-[5-(2,6-dimethylphenyl)-1-methyl-1-pentenyl]imidazole
4-[3-(2,6-dimethylphenyl)-2-methyl-1-propenyl]imidazole
4-[2-(2,6-dimethylphenyl)-1-ethylethenyl]imidazole
4-[2-(2,3-dimethylphenyl)-1-methylethenyl]imidazole
4-[2-(2,6-dimethylphenyl)-1-isopropylethenyl]imidazole
4-[2-(2,6-dimethylphenyl)-1-methylethenyl]-2-methylimidazole
4-[2-(2,6-dimethylphenyl)-1-methylethenyl]-5-methylimidazole
4-[2-(2,6-dichlorophenyl)-1-methylethenyl]imidazole
4-[5-(2,6-dimethylphenyl)-1-methyl-1-pentenyl]imidazole
4-[3-(2,6-dimethylphenyl)-1-ethyl-1-propenyl]imidazole
4-[5-(2,6-dimethylphenyl)-1-methyl-1-pentenyl]-5-methylimidazole
4-[5-(2,6-dimethylphenyl)-1-methylpentyl]imidazole
4-[4-(2,6-dichlorophenyl)-1-methyl-1-butenyl]imidazole
4-[2-(2,6-dimethylphenyl)-1-ethylethyl]imidazole
4-[2-(2,6-dimethylphenyl)-2-ethylethyl]imidazole
4-[2-(3,4-methylenedioxyphenyl)propyl]imidazole
4-[2-(2-bromo-4,5-methylenedioxyphenyl)propyl]imidazole The compounds of the present invention have been found to possess excellent antihypertensive activity. Preliminary tests have shown that they also possess other valuable pharmacological properties, for example, antithrombotic and diuretic effect. Antimycotic and antifungal properties have also been found.

While all of the compounds of formula (I) and (II) essentially satisfy the objectives of the present invention, certain groups of compounds remain preferred. One such preferred group is represented by formula (I) wherein $R_4$ is hydrogen, $R_3$ is alkyl and $R_5$, $R_6$ and $R_7$, which can be the same or different, each are hydrogen, methyl, ethyl or halogen. Another preferred group of compounds is represented by formula (II), wherein $R_5$, $R_6$ and $R_7$, which can be the same or different, each are hydrogen, methyl, ethyl or halogen. In such compounds, those in which $R_1$ is hydrogen or methyl, $R_2$ is hydrogen or methyl, $R_8$ or $R_{11}$ is methyl, ethyl or isopropyl, $R_9$ and $R_{10}$ are hydrogen and n is 0 may be mentioned. Especially the compounds wherein n is greater than 0 possess valuable antimycotic properties. Especially good antihypertensive properties have been found in compounds of formula (II) wherein n is 0 and X is

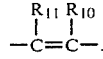

According to the feature of the invention, the compounds of formula (I) wherein $R_4$ is OH and the compounds of formula (II) are made by a Grignard reaction, in which an imidazolylketone of the formula

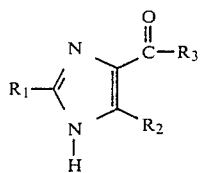

wherein $R_1$, $R_2$ and $R_3$ are as defined before, is reacted with an arylalkyl magnesium halide derivative or aryl magnesium halide derivative of the formula:

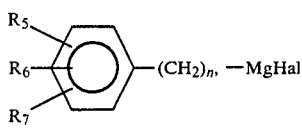

wherein $R_5$, $R_6$ and $R_7$ are as defined before, n' is 0 to 5 and Hal is a halogen atom to give compounds of the formula (III)

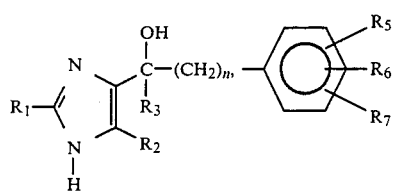

wherein $R_1$, $R_2$, $R_3$, $R_5$, $R_6$, $R_7$ and n' are as before.

The arylalkylmagnesium halide derivative can be, for example, an arylalkylmagnesiumbromide derivative, which is prepared by reacting the corresponding arylalkylbromide derivative with magnesium. Suitable solvents for the reaction include a variety of ethers, preferably tetrahydrofuran. The arylalkylmagnesiumhalide derivative is prepared in the usual way by adding the arylalkylmagnesiumhalide derivative in a suitable solvent, e.g. tetrahydrofuran, dropwise onto magnesium turnings covered by tetrahydrofuran, at the boiling point of the reaction mixture. When the magnesium turnings have reacted, the mixture is cooled slightly and the 4-imidazole derivative is added in solid form in small portions or in tetrahydrofurane solution. After the addition, the reaction mixture is refluxed until all of the 4-imidazole derivative has reacted. The reaction time varies between one and five hours.

Another process for the preparation of compounds of formula (III) is a Grignard reaction in which a compound of the formula (IV)

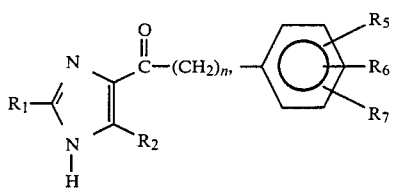

wherein $R_1$–$R_7$ and n' are as before, is reacted with a compound of the formula $R_3MgHal$ wherein $R_3$ is an alkyl or aryl as defined before and Hal is halogen. Yet another process for the preparation of compounds of formula (III) is a Grignard reaction in which an imidazole carboxylic acid alkyl ester, preferably the methyl ester of the formula

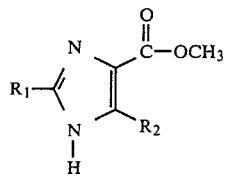

wherein $R_1$ and $R_2$ are as before, is reacted in a first step/with a Grignard reagent of the formula

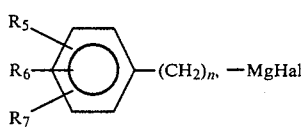

wherein $R_5$, $R_6$, $R_7$ and n' are as before, to give a compound of formula (IV), which in a second step without isolation is reacted with a Grignard reagent of the formula $R_3MgHal$ wherein $R_3$ is as defined before.

Compounds of formula (I) wherein $R_4$ is H can be prepared by reduction of compounds of formula (III) wherein n' is 0 with hydrogen. A suitable catalyst is e.g. palladium-on-carbon.

Unsaturated compounds of formula (I) wherein $R_3$ and $R_4$ are =$CH_2$, =CH—$CH_3$, =CH—$CH_2CH_3$, $$=C\begin{matrix}CH_3\\CH_3\end{matrix}$$

or =CH—$CH_2CH_2CH_3$ or formula (II) wherein $R_{10}$ is hydrogen are prepared by dehydrating compounds of formula (III):

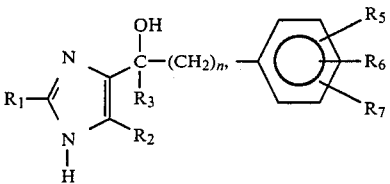

wherein $R_1$, $R_2$, $R_5$, $R_6$, $R_7$ are as defined before, $R_3$ is an alkyl or aryl as defined before and n' is 0 to 5, to give a compound of the formula (V)

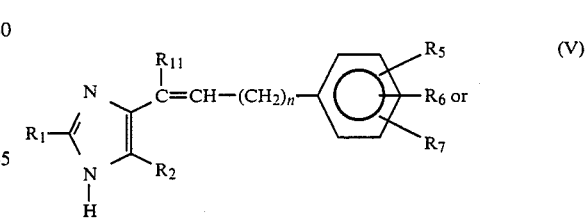

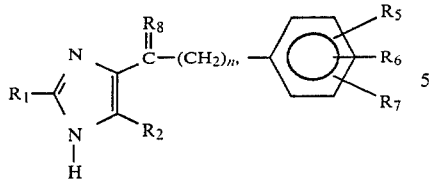

wherein $R_1$, $R_2$, $R_5$, $R_6$, $R_7$, and n and n' are as defined before; $R_{11}$ is an alkyl as defined before and $R_8$ is an alkenyl as defined before.

The dehydration is preferably performed by refluxing in an appropriate acidic solution, e.g. concentrated hydrochloric acid or heating for example with potassium-hydrogen sulfate.

The compounds of formula (V) can further be reduced with hydrogen in the presence of a palladium-on-carbon catalyst to the corresponding saturated compounds of formulae (I) and (II).

Compounds of formula (II) wherein $R_{11}$ is hydrogen are prepared by a Wittig reaction which comprises reacting an imidazole aldehyde of the formula

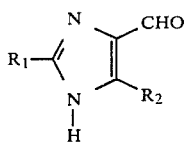

wherein $R_1$ and $R_2$ are as before, with an aralkylidene-triphenylphosphorane of the formula:

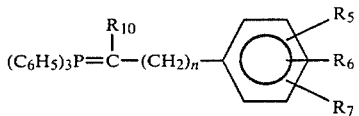

wherein $R_5$, $R_6$, $R_7$, $R_{10}$ and n are as defined before, to give the unsaturated compounds of formula (II), which in a further step can be reduced to the corresponding saturated compounds of formula (II) as described above.

The aralkylidenetriphenylphosphoranes are preferably prepared by reacting the corresponding aralkyltriphenylphosphonium halide of the formula:

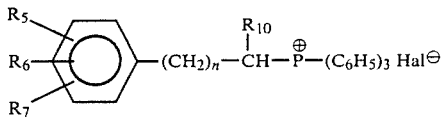

wherein $R_5$, $R_6$, $R_7$, $R_{10}$ and n are as before and Hal is halogen, with a basic reagent, preferably butyllithium.

In the Grignard- and Wittig-syntheses described above, the free nitrogen atom in the imidazole starting material can be protected by different methods. Suitable protecting groups are for example benzyl, triphenylsilyl or dialkoxymethane. The removal of the protecting group can be performed in different ways, and depends on the kind of protecting group used. For example, a dialkoxymethane group is removed by acidic hydrolysis and a benzyl group by sodium in liquid ammonia.

The present invention further provides yet another method for preparing compounds of the invention.

Thus, according to this embodiment of the invention, a starting material of the formula (VI) or (VII)

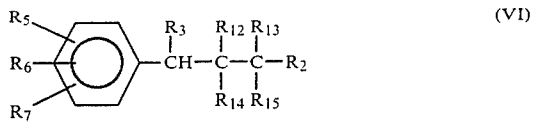

or

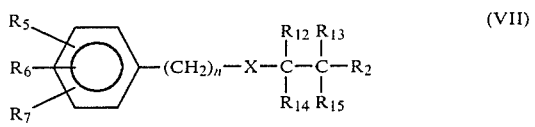

wherein $R_2$, $R_3$, $R_5$, $R_6$, $R_7$ and n are as hereinbefore defined; wherein $R_{12}$, $R_{13}$, $R_{14}$ and $R_{15}$, which can be the same or different, are each hydrogen, hydroxy, mercapto, halogen, amino, —O— alkyl of 1 to 7 carbon atoms or

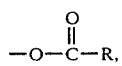

wherein R is an alkyl; or wherein $R_{12}$ and $R_{14}$ can be combined to form a keto group, or $R_{13}$ and $R_{15}$ can be combined to form a keto group, or both $R_{12}$ and $R_{14}$ and $R_{13}$ and $R_{15}$ can simultaneously form keto groups; is reacted with a reagent capable of converting said starting material to the corresponding imidazole of the formula:

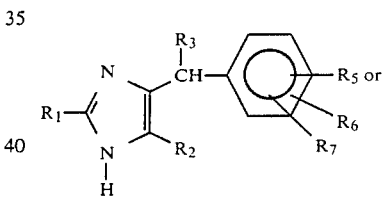

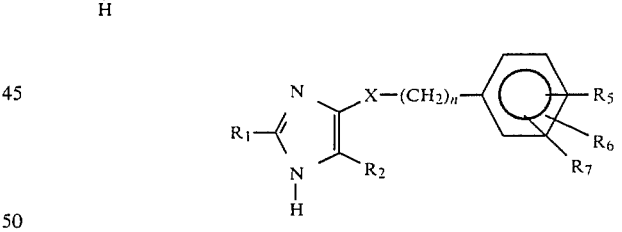

wherein $R_1$, $R_2$, $R_3$, $R_5$, $R_6$, $R_7$, X and n are defined as before. Reagents capable of converting the depicted starting material to the corresponding imdidazole include $NH_3 + CH_2O$ (or a source of ammonia and formaldehyde);

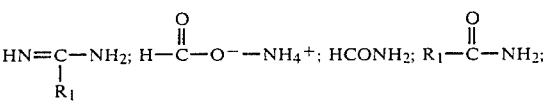

or $R_1CHO$ and $NH_3$. Choice of an appropriate reagent varies with the particular starting material employed.

When $R_1$ is hydrogen it is preferable to employ formamide as the reagent in cases where, in place of the bromine atom in the aforementioned starting materials, there is instead a hydroxyl, amino or acetyl group. In these instances, formamide is used in excess and acts in part as the solvent. Generally, the reaction is run at the boiling point of formamide for a period of time ranging from one to five hours.

Yet another process for the preparation of the compounds of formula (I) and (II) comprises reacting formamide with a benzene derivative of the formula:

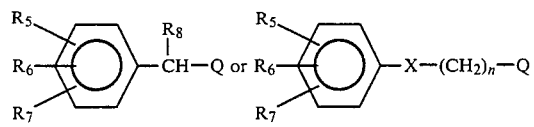

wherein $R_5$, $R_6$, $R_7$, $R_8$, n and X are as defined hereinabove, and Q is a radical of formula:

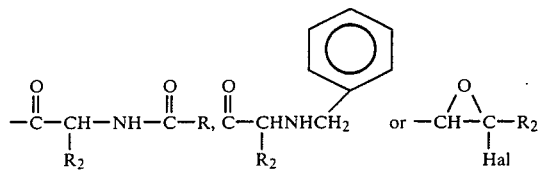

wherein R is a substituted and unsubstituted alkyl, arylalkyl or aryl group, and $R_2$, and Hal are as defined hereinabove. Preferably the reaction is performed by vigorously boiling the benzene derivative in formamide, the reaction time varying with the particular material employed.

Reaction times typically are from 30 minutes to 8 hours. Obviously, the formamide treatment will be followed by reaction with an appropriate acid (e.g. HCl) when Q in the starting material is

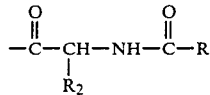

in order to obtain the corresponding compound of formula (I) and (II).

Similarly, when a starting material wherein Q is

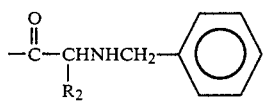

is employed, then the formamide treatment will be followed by hydrogenation, thus affording the desired compound of formula (I) and (II).

A further process for the preparation of the compounds of the formula (I) and (II) comprises hydrolysing a corresponding N-acetylated compound of the formula (I) and (II)

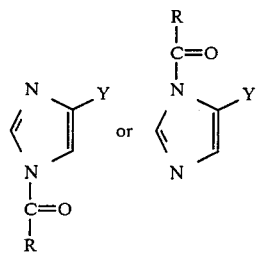

where Y is the arylalkylresidue determined by the formula (I) and (II), R is an alkyl group of 1 to 7 carbon atoms or an aryl radical of 6 to 10 carbon atoms.

Preferably, the hydrolysis is carried out by boiling the starting material, an N-acylated imidazole derivative, in an aqueous solution of an inorganic acid until the reaction is completed.

Yet another process for the preparation of the compounds of formula (I) and (II) comprises hydrogenating a starting material of the formula:

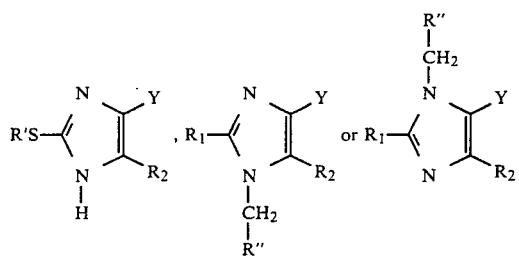

wherein Y is as defined before and R' is an aryl or alkyl and R" is an aryl group. The hydrogenation is conveniently conducted in the presence of a suitable catalyst and under a hydrogen atmosphere, with stirring or using metallic sodium in liquid ammonia. Suitable catalysts include platinum oxide, palladium-on-carbon and Raney nickel. Reaction temperatures vary with the particular starting material employed, with typical temperatures being 25°–70° C.

Yet another method for the preparation of the compounds of formula (I) or (II) wherein X is

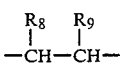

comprises reacting a N-trialkylsilylimidazole of the formula

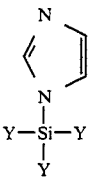

wherein Y is an alkyl group, preferably methyl, with an arylalkylhalogenide of the formulae

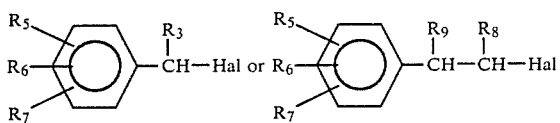

wherein $R_3$, $R_5$, $R_6$, $R_7$, $R_8$ and $R_9$ are as before and Hal is a halogen atom, in the presence of a Lewis acid, for example titanium tetrachloride, aluminium chloride or zinc chloride. As solvent can be used for example methylene chloride or chloroform. The reaction is preferably carried out at room temperature stirring the starting materials for 6–12 hours.

The intermediates of formula (VI) and (VII) can be prepared for example as follows:

An aldehyde of the formula

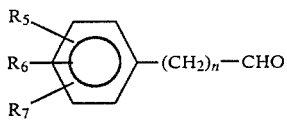

wherein $R_5$, $R_6$, $R_7$ and n are as before, is reacted in alkaline or acidic conditions with a ketone, preferably acetone, to give a compound of the formula (VIII) via direct aldol condensation:

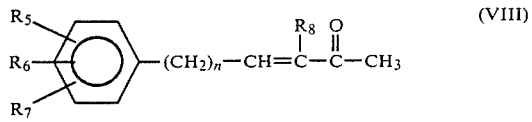

wherein $R_8$ is an alkyl as defined before, which compound in a second step is catalytically reduced to give the corresponding saturated compound of the formula:

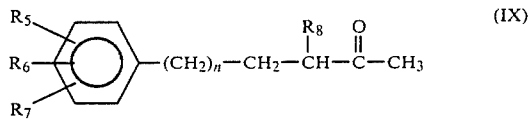

which compound in a third step is regioselectively brominated in methanol to give compounds of formula VII.

Another method for the preparation of the compounds of the general formula (VII) is the regioselective alkylation process of ketones in whih for example a halide compound of the formula (X)

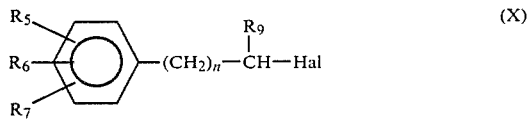

is reacted with a trimethylsilylenolether derivative of the general formula (XI)

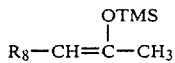

wherein $R_8$ is an alkyl as before, in the presence of a Lewis acid, for example zinc (II) chloride, to give a compound of the formula (XII)

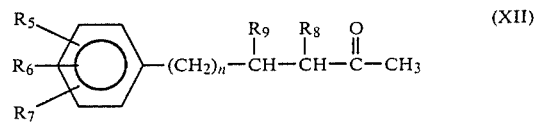

The compound of formula (XII) is further brominated as before to give compounds of the formula (VII).

When $R_8$ and $R_2$ are hydrogen yet another method for the preparation of compounds of the formula (VII) can be applied. In this method a halide of the general formula (XIII)

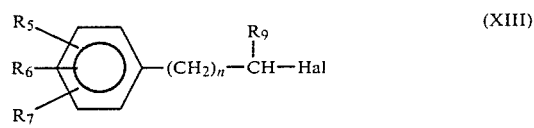

is reacted with lithiated N,N-dimethylhydrazone of acetone followed by hydrolysis to give a compound of the general formula (XIV)

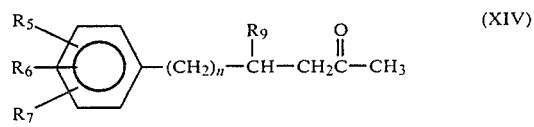

which compounds are brominated as before to give compounds of the formula (VII).

According to another method for the preparation of compounds of the formula (VII), compounds of the formula (VIII) are selectively brominated using as brominating agent for example 2-carboxyethyltriphenylphosphonium perbromide, which has the formula (XV)

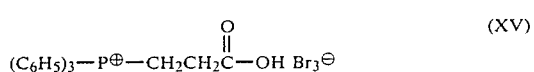

Yet another method for the preparation of compounds of the formula (VII) is possible via a directed aldol condensation, in which for example a compound of the formula (XVI)

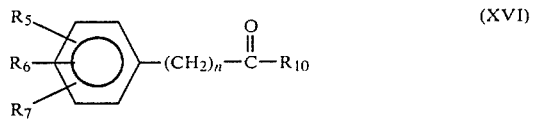

is reacted with the compound (XI) in the presence of a Lewis acid followed by dehydration to give a compound of the formula (XVII)

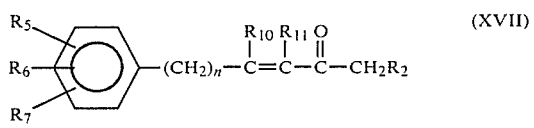

which compound is further brominated as before to give a compound of the formula (VII).

When $R_{11}$ is hydrogen, compounds of the formula (VII) can be prepared from compounds of the formula (XVI), wherein these are reacted with 1-lithiated N,N-dimethylhydrazone of methylalkylketone of the formula (XVIII)

$$LiCH_2-\underset{\underset{N-N(CH_3)_2}{\|}}{C}-CH_2R_2 \qquad (XVIII)$$

Here in the first step compounds of the formula (XIX) are achieved, (XIX) [structure: aryl-(CH$_2$)$_n$-C(R$_{10}$)=CH-C(O)-CH$_2$R$_2$ with R$_5$, R$_6$, R$_7$ substituents on ring]

the bromination of which compounds are performed following the method above.

The preparation of compounds of the general formula (VII) can be accomplished from compounds of the general formula (XVII) by hydrogenation of the carbon-carbon bouble bond as well. The bromination in the second step leads to compounds of the formula (VII).

Alkylation of compounds of the general formula (XVII) when $R_2$ and $R_{10}$ are hydrogen can be accomplished, too. In this method a compound of the formula (XX)

(XX) [structure: aryl-(CH$_2$)$_n$-CH=C(R$_8$)-C(O)-CH$_3$ with R$_5$, R$_6$, R$_7$ substituents]

is reacted with an alkylation reagent such as dialkyllithiocuprate (XXI) which undergoes 1,4-conjugate addition $$(R)_2CuLi \qquad (XXI)$$

to form compounds of the formula (XII).

Condensation of an arylalkylketone or its vinylogue with 4-imidazole aldehydes of the formula (XXII)

(XXII) [imidazole structure with CHO and R$_1$, R$_2$ substituents]

provides further another method for the preparation of compounds according this invention. The condensation is performed for example in aqueous alcohol catalyzed by sodium hydroxide. Arylalkylketones or their vinylogues have the general formulae (XXIII) and (XXIV)

(XXIII) [aryl-C(O)-CH$_2$R$_{10}$ with R$_5$, R$_6$, R$_7$]

(XXIV) [aryl-CH=CH-C(O)-CH$_2$R$_{10}$ with R$_5$, R$_6$, R$_7$]

In the first step this condensation gives unsaturated ketones of the formulae (XXV) and (XXVI)

(XXV) [aryl-C(O)-C(R$_{10}$)=CH-imidazole with R$_1$, R$_2$]

(XXVI) [aryl-CH=CH-C(O)-C(R$_{10}$)=CH-imidazole with R$_1$, R$_2$]

which compounds are then hydrogenated to the end products according to the formulae (XXVII) and (XXVIII)

(XXVII) [aryl-CH$_2$-CH(R$_{10}$)-CH$_2$-imidazole with R$_1$, R$_2$]

(XXVIII) [aryl-CH$_2$CH$_2$CH$_2$CH(R$_{10}$)-CH$_2$-imidazole with R$_1$, R$_2$]

Yet another method for the preparation of compounds of formula (I) wherein $R_4$ is H comprises reacting a compound of the formula

[structure: imidazole-C(=CH)-CH(OR)-aryl with R$_1$, R$_2$, R$_5$, R$_6$, R$_7$]

wherein $R_1$, $R_2$, $R_5$, $R_6$ and $R_7$ are as before and R is an alkyl of 1 to 4 carbon atoms with a Grignard reagent of the formula $$R_3-CH_2MgHal$$

in a mixture of tetrahydrofuran and toluene with refluxing to give a compound of the formula

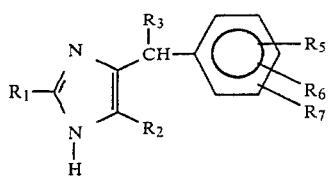

As stated herein above, the compounds of the general formula (I) and (II) and their non-toxic, pharmaceutically acceptable acid addition salts have valuable pharmacological properties and have been found to possess excellent antihypertensive properties.

Tests have shown that they also possess other pharmacological properties as well, for example, antithrombotic activity. Furthermore, antimycotic and antifungal properties have been found, too.

The processes described above for the preparation of compounds of formula (II) wherein X is

result mainly in the trans isomer of the compound. The trans isomer can be converted to the cis isomer according to known methods, e.g. by heating it in the presence of an acid or by irradiating it with ultraviolet light.

Administration of isomeric compounds of formula (I) and (II), their non-toxic, pharmaceutically acceptable salts or mixtures thereof may be achieved parenterally, intravenously or orally. Typically, an effective amount of the derivative is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the derivative is administered, etc., and of course the structure of the derivative.

The pharmaceutical carriers which are typically employed with the derivatives of the present invention may be solid or liquid and are generally selected with the planned manner of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The anti-hypertensive properties of the imidazole derivatives of the present invention have been determined by the following procedure. Sprague-Dawley rats of normal weight were first anesthetized with urethane. After this, the femoral artery was connected by way of a polyethylene tube with a blood pressure transducer. The test substance was then injected into the femoral vein or given intraperitoneally and the blood pressure and the pulse frequency were registered with a recorder.

In a further test for anti-hypertensive properties unanesthetized Wistar spontaneous hypertensive rats (SHR) were used. The test derivative was administered perorally by way of a tube into the stomach. The blood pressure was measured from the tail using an indirect bloodless method.

The diuretic activity was studied in rats by collecting the urine output during 0–5 hours after i.p. injection of the compounds. Before the test the animals were fasting overnight and got 10 ml water p.o. immediately before the injection.

The antithrombotic activity was investigated in vitro. The inhibiting activity of the compounds against ADP- and collagen-induced aggregation of thrombocytes was measured. In the test thrombocytes from a cow was used. To 1.2 ml of plasma containing 250000 thrombocytes/mm$^3$ were added 50 $\mu$l of a solution of the compound to be tested. After 10 min incubation either ADP or collagen was added. The aggregation of the thrombocytes was turbidimetrically determined at $\lambda = 605$ n m.

The antimicrobial activity was determined in vitro according to a qualitative test for antibacterial and antifungal activity, using the agar diffusion method, against the following standard organisms: *Staphylococcus aureus, Streptococcus pyogenes, Escherichia coli, Proteus mirabilis, Pseudomonas aeruginosus, Candida albicans* and *Aspergillus niger.*

The antifungal activity was determined in vitro against the following fungi: *Trichophyton rubrum, Trichophyton mentagrophytis, Microsporum canis, Epidermophyton floccosum,* Chrysosporum, *Candida albicans, Candida guilliermondi* and *Saccaromyces cerevisiae.* The fungi were cultured by plating on an agar nutrient medium. The compound to be tested was added before the incubation. A measure of the efficiency of the compound tested is the radius of the circle, within which the growth of the fungi has been inhibited.

Acute toxicity was determined by using female mice of NMRI-Strain with an age of about 7 months and weighing 30–40 g. The administration of the test compound was i.v.

Thus the compound 4-[2-(2,6-dimethylphenyl)-1-methylethenyl]imidazole, which has a LD$_{50}$ value of 40 mg/kg i.v. in mice, was found in the blood pressure study with anesthetized rats of normal weight described above to cause a registrable lowering of the blood pressure at a dose of 3 $\mu$g/kg i.e. At a dose of 10 $\mu$g/kg i.v. the blood pressure lowering was quite clear and at a dose of 100–300 $\mu$g/kg i.v. the reduction of the blood pressure was on an average 38%. The duration of the effect was at least 30 minutes (after which time the determination was interrupted). A blood pressure lowering of more than 40% was obtained when 2 mg/kg of the compound was administered perorally. The duration of the effect was at least 5 h.

The compound 4-[2-(2,6-dimethylphenyl)-1-methylethyl]imidazole (LD$_{50}$=40 mg/kg i.v. in mice) caused a blood pressure lowering of 20 percent measured 30 minutes after the administration at a dose of 100 $\mu$g/kg i.v. When 10 mg/kg of the compound was given perorally, a blood pressure drop of 25% was obtained. Duration was at least 5 h.

The compound 4-[($\alpha$-methyl)-2,6-dimethylbenzyl]imidazole (LD$_{50}$=150 mg/kg i.v. in mice) caused a blood pressure lowering of 30% at a dose of 1–10 mg/kg i.v. (30 min. after administration).

The compound 4-[(α-methyl)-2,3-dimethylbenzyl]imidazole (LD$_{50}$=40 mg/kg i.v. in mice) caused a blood pressure drop of 55% at 10 μg/kg i.v. (after 30 min.). Given perorally (1 mg/kg) the compound gave a blood pressure drop of 20%. The duration was at least 5 h.

The compound 4-[2-(2,6-dimethylphenyl)propyl]imidazole, which has a LD$_{50}$ value of 200 mg/kg i.v. in mice gave a blood pressure drop of 30% at a dose of 3 mg/kg i.v., measured 30 min. after administration.

The compound 4-[2-(2,6-dimethylphenyl)-2-ethylethyl]imidazole gave a blood pressure drop of about 25% at a dose of 3 mg/kg i.v., measured 30 min. after administration.

The compound 4-[2-(2,6-dimethylphenyl)-1-ethylethenyl]-imidazole which has a LD$_{50}$ value of 110 mg/kg i.v. in mice, gave a blood pressure drop of 35% at a dose of 3 mg/kg intraperitoneally measured 30 min. after administration.

The compound 4-(α-methyl-2-methylbenzyl)imidazole, which has a LD$_{50}$ value of 100 mg/kg i.v. in mice, gave a blood pressure drop of 20% at a dose of 0.3 mg/kg intraperitoneally measured 30 min. after administration.

The compound 4-(α-methyl-2-chlorobenzyl)-imidazole, which has a LD$_{50}$ value of 140 mg/kg i.v. in mice gave a blood pressure drop of about 20% at dose of 10 mg/kg i.v. 30 min. after administration.

The compound 4-[2-(2,6-dichlorophenyl)-1-methylethenyl]imidazole, which has a LD$_{50}$ value of 50 mg/kg i.v. in mice gave a blood pressure drop of 25% at a dose of 0.3 mg/kg i.v. measured 30 min. after administration.

The compound 1-(4-imidazolyl)-1-(2,3-dimethylphenyl)ethylene, which has a LD$_{50}$ value of 100 mg/kg i.v. in mice gave a blood pressure drop of about 40% at a dose of 3 mg/kg i.v. (after 30 min.) A blood pressure drop of 20% was obtained at a dose of 10 mg/kg perorally. The duration was at least 8 h.

The compound 4-(α-ethyl-2,3-dimethylbenzyl)-imidazole, which has a LD$_{50}$ value of 40 mg/kg i.v. in mice gave a blood pressure drop of 40% at a dose of 1 mg/kg i.v. measured 30 min. after administration.

In the antithrombotic test, the compound 4-[2-(2,6-dimethylphenyl)-1-methylethenyl]imidazole inhibited the collagen-induced and the ADP-induced aggregation of thrombocytes completely.

In the diuretic test, the compound 4-[2-(2,6-dimethylphenyl)-1-methylethyl]-imidazole caused an urine output increase of 227% measured 3 h after administration. The dose was 1 mg/kg i.p.

In the same test, the compound, 4-[2-(3,4-methylenedioxyphenyl)propyl]imidazole, which has a LD$_{50}$ value of 170 mg/kg i.v. in mice, caused an urine output increase of 275% at a dose of 1 mg/kg p.o. measured 3 hours after administration. The corresponding value for a dose of 5 mg/kg p.o. was 452%.

The clinical dosage ranges for the compounds of the invention for oral administration of the antihypertensives have been estimated as 0.05 to 1 mg/kg per day.

In the Examples below, where $^1$H-NMR spectrum shifts are presented, the NMR spectra were determined with a Perkin-Elmer R 24 or a Bruker WP80DS apparatus using an external tetramethylsilane standard, from which the presented chemical shifts (δ, ppm) are tabulated. The letters s, d, t and m are used to indicate a singlet, doublet, triplet or multiplet, respectively and coupling constants in hertz when given. In the same connection, the number of hydrogen atoms is also stated. The compounds which are indicated as bases are tested in deuterium methanol, deuterium acetone or deuterium chloroform, while the values for compounds which are indicated as hydrochlorides were determined in deuterium oxide. The presented $^{13}$C-NMR-spectrum were determined with a Bruker WP80DS apparatus.

The mass-spectra were determined with a Perkin-Elmer RMU-6E apparatus using direct inlet system. The temperature employed was the lowest temperature needed for the evaporation of the compound as base. In the examples the strongest and the most essential fragment-ions from a structural viewpoint are given as m/e values. In parenthesis is given the intensity of the fragment-ion in relation to the main peak.

EXAMPLE 1

4-[α,α-bis(2-methylphenyl)hydroxymethyl]-5-methylimidazole 4.9 g (0,2 mol) of dry magnesium turnings are covered with 50 ml of dry tetrahydrofuran. The mixture is heated to boiling and a solution of 34 g (0.2 mol) of 2-bromotoluene in 50 ml dry tetrahydrofuran is added dropwise at such a rate that smooth reaction is maintained. After the addition is complete, the reaction mixture is refluxed for about 30 minutes until the magnesium turnings are no longer react. The reaction mixture is then cooled to about 50° C. and 9,3 g of 5-methyl-4-imidazole carboxylic acid methyl ester are added in small portions. After the addition is complete, the mixture is refluxed for another 2 hours and the solvent is then distilled off to give about half of the original volume. The mixture is cooled and poured into 300 ml of cold water containing 15 ml of concentrated sulfuric acid, with agitation. The stirring is continued for an additional 15 minutes and the mixture is then filtered. The precipitate, filtered from the acidic water, which is the sulfate salt of the compound, is extracted to chloroform from basic water-ethanol solution. After evaporation, the crude product is recrystallized from acetone, m.p. 169°–171° C.

$^1$H-NMR (HCl-salt): 1.7 (s, 3H), 2.1 (s, 6H), 4.7 (s, 2H), 7.1 (m, 8H), 8.7 (s, 1H).

MS: 292 (55%), 274 (69%), 259 (100%), 232 (7%), 217 (9%), 201 (52%), 199 (72%), 167 (18%), 109 (63%).

EXAMPLE 2

4-[α,α-bis(2-methylphenyl)hydroxymethyl]imidazole

A Grignard reagent is prepared from 68,4 g of o-bromotoluene and 9,6 g of Mg-turnings in 200 ml of THF. To this solution 12,6 g of 4-imidazole carboxylic acid methylester are added at 50° C. and the reaction mixture is refluxed for 5 hours.

The mixture is then poured into cold water, which includes 60 ml of conc. HCl. The hydrochloride of the product is filtered off, washed with chloroform and recrystallized from isopropanol; yield 23 g (73%), m.p. 178°–179° C. Liberation of hydrochloride is achieved in water-ethanol with sodiumhydroxide; m.p. 138°–140° C.

$^1$H-NMR (HCl-salt): 1.9 (s, 6H), 4.6 (s, 3H), 6.7 (s, 1H), 7.0 (s, 8H), 8.7 (s, 1H).

EXAMPLE 3

4-(α,α-diphenyl)hydroxymethyl-5-methylimidazole

The compound is prepared by the method described in Example 2 except that bromobenzene is used in place of o-bromotoluene and 5-methyl-4-imidazole carboxylic acid methyl ester in place of 4-imidazolecarboxylic acid methyl ester; yield 18,5 g (70%), m.p. 188°–190° C. (as base from ethanol).

¹H-NMR: 1.4 (s, 3H), 4.7 (s, 2H), 7.0 (s, 10H), 7.2 (s, 1H).

MS: 264 (80%), 246 (78%), 231 (28%), 218 (20%), 204 (9%), 187 (100%), 109 (64%), 105 (26%), 77 (34%).

EXAMPLE 4

4-[[-α-(2-methylphenyl)]-2-methylbenzyl]imidazole

The starting material, 4-[α,α-bis(2-methylphenyl)hydroxymethyl]imidazole is dissolved in 100 ml of acetic acid. 100 mg of Pd/C are added and the reaction mixture is stirred vigorously in a hydrogen atmosphere at about 60° C. until the reaction is completed. The mixture is then filtered and distilled to a smaller volume. 70 ml of water are added and that mixture is then washed twice with 20 ml portions of chloroform. The aqueous phase is made alkaline with NaOH and extracted with chloroform (3×40 ml). The combined chloroform extracts are washed with water (1×10 ml) and dried over Na₂SO₄. The solution is evaporated to dryness. Yield 93%, m.p. 228°–231° C. (from ethanol). Hydrochloride in ethyl acetate-isopropanol: m.p. 245°–254° C.

¹H-NMR: 2.1 (s, 6H), 4.7 (s, 2H), 5.8 (s, 1H), 6.6 (s, 1H), 6.9 (m, 8H), 8.7 (s, 1H)

EXAMPLE 5

4-(α-phenylbenzyl)-5-methylimidazole

The compound is prepared from 4-(α,α-diphenyl)hydroxymethyl-5-methylimidazole according to the method in Example 4. Yield 69%, m.p. 198°–204° C. (from ethanol).

¹H-NMR: 1.6 (s, 3H), 4.5 (s, 1H), 5.3 (s, 1H), 6.8 (s, 10H), 7.3 (s, 1H).

EXAMPLE 6

4-[α-(2-methylphenyl)-α-(2-methylbenzyl)]-5-methylimidazole

The compound is prepared according to the method in Example 4 using 4-[α,α-bis-(2-methylphenyl)hydroxymethyl]-5-methylimidazole as starting material. Yield 79%, m.p. 178°–180° C. (from water-ethanol).

¹H NMR: 1.4 (s, 3H), 1.8 (s, 6H), 4.6 (s, 1H), 5.35 (s, 1H), 7.1 (m, 8H), 7.15 (s, 1H).

EXAMPLE 7

4-[[α-(2,3-dimethylphenyl)-α-methyl]hydroxymethyl]imidazole, 1-(4-imidazolyl)-1-(2,3-dimethylphenyl)ethylene and 4-(α-methyl-2,3-dimethylbenzyl)imidazole For the preparation of 2,3-dimethylmagnesiumbromide in the first step, 4,9 g of dry magnesium turnings are covered with 50 ml of dry tetrahydrofuran.

The mixture is heated to boiling and a solution of 37 g of 2,3-dimethylbromobenzene in 50 ml dry of tetrahydrofuran is added dropwise at such a rate that a smooth reaction is maintained. After the addition is complete the reaction mixture is refluxed for about 30 minutes until the magnesium turnings no longer react.

In the same way in another flask of methylmagnesiumbromide is prepared from 2.4 g of magnesium turnings and 9.5 g of methylbromide in tetrahydrofuran.

Yet another flask of 12,6 g of 4-imidazolecarboxylic acid methylester, is added to 100 ml of dry tetrahydrofuran and the mixture is stirred while heating to about 50° C. To this is then dropped the earlier prepared 2,3-dimethylmagnesiumbromide solution and immediately after that the methylmagnesiumbromide solution. To complete the reaction, the mixture is refluxed for several hours. The solvent is then distilled off to give about half of the original volume. The mixture is cooled and poured into 350 ml of cold water containing 50 ml of concentrated sulfuric acid, with agitation. The stirring is continued for an additional 15 minutes and the mixture is then filtered.

The pH of the filtrate is adjusted slightly basic and the mixture is extracted three times with 50 ml portions of methylene chloride. The combined methylene chloride extracts are washed with water and evaporated to dryness. The residue which contains crude 4-[[α-(2,3-dimethylphenyl)α-methyl]hydroxymethyl]imidazole is further purified column chromatographically in silicagel using chloroform methanol as eluent. 1-(4-imidazolyl)-1-(2,3-dimethylphenyl)-ethylene is then obtained from the above product by heating it with potassiumhydrogen sulphate at 136° C.

¹H-NMR (HCl-salt): 2.104 (s, 3H), 2.313 (s, 3H), 5.187 (s, 2H), 5.358 (s, 1H), 6.106 (s, 1H), 7.03–7.22 (m, 4H), 8.98 (s, 1H).

¹³C-NMR (HCl-salt): Signals at ppm: 18.073, 21.857, 118.789, 119.455, 127.961, 129.475, 132.230, 135.802, 136.498, 136.892, 137.921, 139.949, 140.070.

Melting point as base: 137°–140° C.

4-(α-methyl-2,3-dimethylbenzyl)imidazole is obtained by hydrogenation with palladium-on-carbon catalyst in 2-N HCl according to the method desribed before.

¹H-NMR (HCl-salt): 1.708 (d, 3H), 2.370 (broad s, 3H), 4.688 (q, 1H), 4.933 (s, 2H), 7.079–7.263 (m, 3H), 7.361 (s, 1H), 8.780 (s, 1H).

¹³C-NMR (HCl-salt): Signals at ppm: 16.529, 21.917, 22.462, 34.662, 117.881, 126.660, 128.385, 131.079, 135.650, 136.952, 140.161, 140.163, 142.855.

By the same method for example the following compounds were prepared:

4-(α-methyl-2,6-dimethylbenzyl)imidazole, M.p. (oxalate): 98°–99° C.

4-(α-ethyl-2,3-dimethylbenzyl)imidazole, M.p. (HCl-salt): 175°–177° C.

4-(α-butyl-2-methylbenzyl)imidazole.

4-(α-methyl-2,3-dimethylbenzyl)-2-methylimidazole.

EXAMPLE 8

4-(2,6-dimethylphenyl)-3-buten-2-one 13.4 g (0,1 mol) of 2,6-dimethylbenzaldehyde, 100 ml of acetone, 100 ml of water and 2 g of calcium hydroxide are mixed together and refluxed for about 20–25 h with agitation. The precipitate is filtered off from the cold reaction mixture. 1 l of ice water is added to the filtrate with agitation. The product is crystallized at a yield of about 90%. M.p. of the recrystallized product: 34°–35° C.

¹H-NMR: 7.55 (1Hd, 16.5), 7.00 (3Hs), 6.26 (1Hd, 16.5), 2.37 (3Hs), 2.31 (6Hs).

EXAMPLE 9

4-(2,6-dimethylphenyl)-2-pentanone

To a mixture containing 20 g of CuI and 50 ml of tetrahydrofuran (THF) are added 105 ml of methyllithium dropwise during with agitation in a nitrogen atmosphere at a temperature of 0° C. or lower until the yellow precipitate barely dissolves. Then 8,7 g of 4-(2,6- dimethylphenyl)-3-buten-2-one in 50 ml of THF are added slowly at 0° C. The stirring is continued for an additional 2 h with a gradual increase of the temperature to +25° C. The reaction mixture obtained is hydrolysed with 300 ml of a solution of NH₄Cl. The ether layer is removed, dried and evaporated to give the crude product.

¹H-NMR: 6.85 (3Hs), 3.78 (1Hq+t, 7.5), 2.76 (2Hd, 7.5), 2.34 (6Hs), 1.99 (3Hs), 1.27 (3Hd, 7.5).

According to the same method, the compound 4-phenyl-2-pentanone was prepared.

¹H-NMR: 7.10 (5Hs), 3.26 (1Hq+t, 7.5), 2.62 (2Hd, fine structur), 1.94 (3Hs, 1.20 (3Hd, 7).

Similarly 4-(3,4-dimethylenedioxyphenyl)-2-pentanone.

¹H-NMR: 6.62 (3H, s), 5.83 (2H, s), 3.20 (1Hq+t, 7), 2.67 (2H, d7), 2.04 (3Hs), 1.26 (3Hd7).

EXAMPLE 10

1-bromo-4-(2,6-dimethylphenyl)-2-pentanone

To 3,8 g of 4-(2,6-dimethylphenyl)-2-pentanone in 25 ml of dry methanol 1.04 ml of bromine are added dropwise rapidly at a temperature not higher than +5° C. Stirring is continued until the bromine colour disappears, while the temperature slowly rises to +20° C. After evaporation the product is obtained at a yield of at least 70%.

¹H-NMR: 6.98 (3Hs), 3.80 (1Hm), 3.67 (2Hs), 3.02 (2Hd), 2.35 (6Hs), 1.33 (3Hd, 7).

According to the same method the compounds 1-bromo-4-phenyl-2-pentanone and 1-bromo-4-(2,6-dimethylphenyl)-3-methyl-2-butanone were prepared.

Similarly using two equivalents of bromine:

1-bromo-4-(2-bromo-4,5-methylenedioxyphenyl)-2-pentanone.

¹H-NMR: 6.9 (1H, s), 6.67 (1H, s), 5.87 (2Hs), 3.80 (2Hs), 2.9 (3Hm), 1.19 (3Hd7).

EXAMPLE 11

4-[2(2,6-dimethylphenyl)propyl]imidazole 5.4 g of 1-bromo-4-(2,6-dimethylphenyl)-2-pentanone, 50 ml of formamide and 5 ml of water are refluxed with stirring for 3 h. The mixture is poured into 300 ml of water (pH 4–5), washed with ether, neutralized with NaHCO₃ and extracted with methylene chloride. After drying and evaporation 2.5 g of product are obtained. This is dissolved in ethyl acetate and HCl/ethylacetate is added. The product is evaporated to dryness, washed with ether, dissolved in water, neutralized with NaHCO₃ and extracted with methylene chloride. The evaporation residue is dissolved in ethyl acetate and the final product is precipitated as oxalate or hydrochloride. M.p. of the hydrochloride 194°–198° C.

¹H-NMR (HCl-salt): 8.70 (1Hs), 6.9 (4Hs), 3.65 (1Hm), 3.21 (2H,d 8), 2.39 (6H broad s), 1.45 (3Hd 7).

According to the same method, the following compounds were prepared: 4-[2-(2,6-dimethylphenyl)-1-methylethyl]imidazole. M.p. of the oxalate 161°–5° C.

¹H-NMR (oxalate): 8.75 (1H broad s), 7.05 (1Hs), 7.00 (3Hs), 3.0 (3Hm), 2.20 (6Hs), 1.31 (3Hd).

4-(2-phenylpropyl)imidazole (as oxalate)

¹H-NMR: 8.52 (1Hs), 7.22 (5Hs), 6.97 (1Hs), 3.05 (3Hm), 1.35 (3Hd) M.p. of the oxalate: 166°–168° C.

4-[2-(3,4-methylenedioxyphenyl)propyl]imidazole

¹H-NMR (as oxalate): 8.70 (1H, s), 7.11 (1H, s), 6.78 (3H, m), 5.95 (2H, s), 3.08 (3H, m), 1.40 (3H, d).

M.p. of oxalate: 154°–156° C.

4-[2-(2,6-dimethylphenyl)butyl]imidazole

M.p. of oxalate 176°–9° C.

¹H-NMR: 8.25 (1H, broad s), 6.95 (3H, s), 6.68 (1H, s), 3.2 (3H, m), 2.45 (3H, s), 2.6–2.0 (2H, m), 2.06 (3H, s), 1.87 (3H, t)

4-[2-(2-bromo-4,5-methylenedioxyphenyl)propyl]imidazole

4-[2-(2,3-dimethylphenyl)propyl]imidazole, M.p. (base): 109°–120° C.

¹H-NMR: 1.25 (d, 3H), 2.17 (s, 3H), 2.24 (s, 3H), 3.0 (d, 2H), 3.5 (m, 1H), 5.26 (s, H₂O), 7.0 (m, 3H), 8.09 (s, 1H), 8.65 (s, 1H).

EXAMPLE 12

4-(2,6-dimethylphenyl)-3-methyl-3-buten-2-one

A mixture of 13.4 g of 2,6-dimethylbenzaldehyde and 15 ml of 2-butanone is saturated with gaseous HCl with stirring. The starting temperature is 0° C., and it is raised to 20°–25° C. in 2 h. The reaction mixture is poured into 0,5 l of cold water, extracted with toluene and washed with a NaHCO₃-solution. The dried toluene extract is filtered, toluene and free 2-butanone are distilled off. The product is obtained by crystallization from di-isopropylether. M.p. 43°–44° C.

¹H-NMR: 7.38 (1Hs), 6.98 (3Hs), 2.42 (3Hs), 2.11 (6Hs), 1.59 (3Hd, 1.4).

EXAMPLE 13

1-bromo-4-(2,6-dimethylphenyl)-3-methyl-3-buten-2-one

To a mixture of 3,8 g of 4-(2,6-dimethylphenyl)-3-methyl-3-buten-2-one in 50 ml of THF a solution of 13 g of 2-carboxyethyltriphenylphosphoniumperbromide in 50 ml of THF is added dropwise at room temperature.

Stirring is continued for another 2 h. 200 ml of water and 100 ml of ligroin are added. The organic layer is washed with a Na₂CO₃-solution and water. After filtration and evaporation 5,5 g of crude product containing 85–90% of 1-bromo-4-(2,6-dimethylphenyl)-3-methyl-3-buten-2-one are obtained.

¹H-NMR: 7.51 (1H broad s), 7.05 (3Hs), 4.27 (2Hs), 2.18 (6Hs), 1.68 (3Hd, 1.3)

EXAMPLE 14

4-[2-(2,6-dimethylphenyl)-1-methylethenyl]imidazole E-isomer

The compound is prepared according to the method described in Example 12, except that 1-bromo-4-(2,6-dimethylphenyl)-3-methyl-3-buten-2-one is used instead of 1-bromo-4-(2,6-dimethylphenyl)-2-pentanone. M.p. of the hydrochloride 260°–262° C.

¹H-NMR: 8.82 (1H, d), 7.36 (1H, d), 7.20 (1H, broad s), 7.08 (3Hs), 2.20 (6Hs), 1.82 (3H,d,1.2).

Using the same method the following compounds were prepared:

4-[2-(2,6-dichlorophenyl)-1-methylethenyl]imidazole. M.p. of the hydrochloride 210°–212° C.

1H-NMR (HCl-salt): 1.9 (s, 3H), 4.6 (broad signal, H2O), 6.85 (s, 1H), 7.0-7.4 (m, 1+3H), 7.6 (s, 1H).

4-[2-(2,6-dimethylphenyl)-1-ethylethenyl]imidazole. M.p. of the hydrochloride 257°-258° C.

1H-NMR (HCl-salt): 1.1 (t, 3H), 2.35 (s, 6H), 2.4 (q, 2H), 4.8 (broad signal, H2O), 7.1 (2×s, 3+1H), 7.65 (s, 1H), 8.95 (s, 1H).

4-[2-(2,6-dimethylphenyl)-1-methylethenyl]-5-methylimidazole. M.p. of the hydrochloride 250°-252° C.

EXAMPLE 15

4-(α-methyl-2,6-dimethylbenzyl)imidazole

To a mixture of N-(trimethylsilyl)imidazole (1.4 g) and titanium tetrachloride (1.6 ml) in dry chloroform (20 ml) a solution of 1-chloro-1-(2,6-dimethylphenyl)ethane (1.7 g) in dry chloroform (10 ml) was added. After stirring for 5 h at room temperature the product mixture was poured onto water, washed with ether and neutralized with sodium hydrogen carbonate. Filtration and extraction with methylene chloride gave 4-[(α-methyl)-2,6-dimethylbenzyl]imidazole, yield 33%.

1H-NMR: δCDCl3 11.4 (1H, broad), 7.19 (1H, s), 6.83 (3H, s), 6.56 (1H, s), 4.52 (2H,q 6), 2.11 (6H, s), 1.63 (3H,d 6).

M.p. of the hydrochloride: 208°-10° C.

13C-NMR (as hydrochloride): δCD3OD 139.8 (1C, s), 139.1 (1C, s), 137.6 (2C, s), 134.9 (1C, d), 130.8 (2C, d), 128.4 (1C, d), 116.6 (1C, d), 32.8 (1C, d), 20.6 (2C, q), 17.0 (1C, q).

Using the same method the following compounds were prepared:

4-(α-methyl-2-methylbenzyl)imidazole. M.p. of the hydrochloride 156°-160° C.

1H-NMR (HCl-salt): 1.63 (d, 3H), 2.40 (s, 3H), 4.52 (q, 1H), 5.10 (s, H2O), 6.9-7.2 (m, 3H), 7.36 (s, 1H), 8.83 (d, 1H).

4-(α-methyl-2,3-dimethylbenzyl)imidazol

13C-NMR (HCl-salt): 16.529, 21.917, 22.462, 34.662, 117.881, 126.660, 128.385, 131.079, 135.650, 136.952, 140.161, 140.161, 142.855.

4-(α-methyl-2-chlorobenzyl)imidazole. M.p. of the oxalate 214°-216° C.

EXAMPLE 16

4-(α-ethyl-2,3-dimethylbenzyl)imidazole 6.0 g of 4-[α-(2,3-dimethylphenyl)ethoxymethyl]-imidazole is dissolved in toluene. To this solution is then added 22.8 g of ethylmagnesiumbromide in tetrahydrofuran and the mixture is refluxed for 20 hours. The mixture is then poured into cold hydrochloric acid and most of the organic solvents is evaporated. The mixture is extracted with methylene chloride. The extract is washed with water, dilute sodium hydroxide solution and water and evaporated to dryness.

The residue, which is crude product is further purified by liquid chromatography by using a column of silica gel and chloroform-methanol as eluent. After liquid chromatographic purification the product melts at 173°-176° C. as hydrochloride.

We claim:

1. A substituted imidazole of the formula:

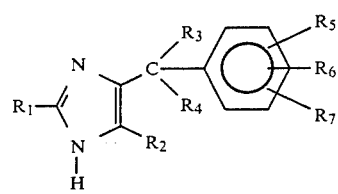

or a non-toxic pharmaceutically acceptable addition salt thereof, wherein $R_1$ is H, alkyl of 1 to 4 carbon atoms or $-CH_2OH$; $R_2$ is H or $-CH_3$; $R_3$ is $-CH_3$, $-CH_2CH_3$, $-CH_2CH_2CH_3$,

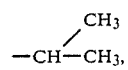

$-CH_2CH_2CH_2CH_3$, or $-CH_2CH=CH_2$, and $R_4$ is H or OH; or $R_3$ and $R_4$ together represent $=CH_2$, $=CH-CH_3$, $=CH-CH_2-CH_3$,

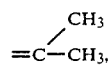

or $=CH-CH_2CH_2CH_2CH_3$; $R_5$ $R_6$ and $R_7$ which can be the same or different are H, $-CH_3$, $-CH_2CH_3$, halogen, OH or $-OCH_3$, at least one of $R_5$, $R_6$ and $R_7$ being other than hydrogen, or $R_5$ is hydrogen and $R_6$ and $R_7$ together form an $-O-CH_2-O-$ bridge between two adjacent carbon atoms in the phenyl group.

2. A compound of formula (I) according to claim 1 wherein each of $R_5$, $R_6$ and $R_7$, which can be the same or different, is hydrogen, methyl, ethyl or halogen, at least one of $R_5$, $R_6$ and $R_7$ being other than hydrogen.

3. A compound of formula (I) according to claim 1, wherein $R_4$ is hydrogen and $R_3$ is methyl, ethyl, propyl, isopropyl or butyl.

4. A compound of formula (I) according to claim 3 wherein $R_1$ is methyl.

5. A compound according to claim 1 which is 4-[(α-methyl)-2,6-dimethylbenzyl]imidazole or a non-toxic pharmaceutically acceptable acid addition salt thereof.

6. A cmpound according to claim 1 which is 4-[(α-methyl)-2,3-dimethylbenzyl]imidazole or a non-toxic pharmaceutically acceptable acid addition salt thereof.

7. A compound according to claim 1 which is 4-[(α-methyl)-2-methylbenzyl]imidazole or a non-toxic pharmaceutically acceptable acid addition salt thereof.

8. A compound according to claim 1 which is 4-[(α-methyl)-2-chlorobenzyl]imidazole or a non-toxic pharmaceutically acceptable acid addition salt thereof.

9. A compound according to claim 1 which is 4-[(α-ethyl)-2,3-dimethylbenzyl]imidazole or a non-toxic pharmaceutically acceptable acid addition salt thereof.

10. A compound according to claim 1 which is 1-(4-imidazolyl)-1-(2,3-dimethylphenyl)-ethylene or a non-toxic pharmaceutically acceptable acid addition salt thereof.

11. A pharmaceutical composition useful for producing an anti-hypertensive effect comprising an effective amount of a substituted imidazole of the formula:

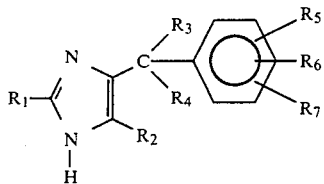

(I)

or a non-toxic pharmaceutically acceptable acid addition salt thereof, wherein $R_1$ is H, alkyl of 1 to 4 carbon atoms or —$CH_2OH$; $R_2$ is H or —$CH_3$; $R_3$ is —$CH_3$, —$CH_2CH_3$, —$CH_2CH_2CH_3$,

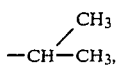

—$CH_2CH_2CH_2CH_3$, or —$CH_2CH$=$CH_2$, and $R_4$ is H or OH; or $R_3$ and $R_4$ together represent =$CH_2$, =$CH$—$CH_3$, =$CH$—$CH_2$—$CH_3$,

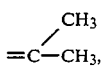

or =$CH$—$CH_2CH_2CH_2CH_3$; $R_5$ $R_6$ and $R_7$ which can be the same or different are H, —$CH_3$, —$CH_2CH_3$, halogen, OH or —$OCH_3$, at least one of $R_5$, $R_6$ and $R_7$ being other than hydrogen, or $R_5$ is hydrogen and $R_6$ and $R_7$ together form an —O—$CH_2$—O—bridge between two adjacent carbon atoms in the phenyl group, and a compatible, pharmaceutically acceptable carrier therefor.

12. A method of producing an anti-hypertensive effect in a subject in whom such an effect is desired which comprises administering thereto an amount effective as an antihypertensive agent of a substituted imidazole as defined in claim 1 or of a non-toxic pharmaceutically acceptable acid addition salt thereof.

* * * * *